US012318120B2

(12) United States Patent
Biedermann et al.

(10) Patent No.: US 12,318,120 B2
(45) Date of Patent: Jun. 3, 2025

(54) BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Berthold Dannecker, St. Georgen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 196 days.

(21) Appl. No.: 17/848,793

(22) Filed: Jun. 24, 2022

(65) Prior Publication Data

US 2022/0395299 A1 Dec. 15, 2022

Related U.S. Application Data

(63) Continuation of application No. 17/394,748, filed on Aug. 5, 2021, now Pat. No. 11,406,426.

(60) Provisional application No. 63/061,475, filed on Aug. 5, 2020.

(30) Foreign Application Priority Data

Aug. 5, 2020 (EP) .................................... 20189703

(51) Int. Cl.
*A61B 17/70* (2006.01)
*A61B 17/00* (2006.01)

(52) U.S. Cl.
CPC ...... *A61B 17/7037* (2013.01); *A61B 17/7032* (2013.01); *A61B 2017/00858* (2013.01)

(58) Field of Classification Search
CPC ............ A61B 17/7037; A61B 17/7032; A61B 2017/00858
See application file for complete search history.

(56) References Cited

U.S. PATENT DOCUMENTS

| 6,835,196 | B2 | 12/2004 | Biedermann et al. |
| 11,464,546 | B2 * | 10/2022 | Biedermann ...... A61B 17/7037 |
| 2005/0222570 | A1 | 10/2005 | Jackson |
| 2006/0036252 | A1 | 2/2006 | Baynham et al. |
| 2006/0100622 | A1 | 5/2006 | Jackson |
| 2008/0132957 | A1 | 6/2008 | Matthis et al. |
| 2010/0211114 | A1 | 8/2010 | Jackson |
| 2011/0160779 | A1 | 6/2011 | Schlaepfer et al. |
| 2014/0277158 | A1 | 9/2014 | Spratt et al. |

(Continued)

FOREIGN PATENT DOCUMENTS

| DE | 20 2004 009073 U1 | 9/2004 |
| EP | 2 893 890 A1 | 7/2015 |

OTHER PUBLICATIONS

Extended European Search Report for Application No. 20189703.0, mailed Feb. 10, 2021, 9 pages.

*Primary Examiner* — Andrew Yang
(74) *Attorney, Agent, or Firm* — Womble Bond Dickinson (US) LLP

(57) ABSTRACT

An anchoring element includes a shank for anchoring to bone and a separate head that is connectable to the shank. The head has an exterior surface with a spherically-shaped section and an unthreaded tool engagement surface that is engageable with a drive tool when the head and the shank are connected to one another.

20 Claims, 16 Drawing Sheets

(56) References Cited

U.S. PATENT DOCUMENTS

2014/0277189 A1    9/2014  Spratt et al.
2016/0278832 A1*  9/2016  Segawa .............. A61B 17/7037
2020/0030006 A1    1/2020  Errico et al.

* cited by examiner

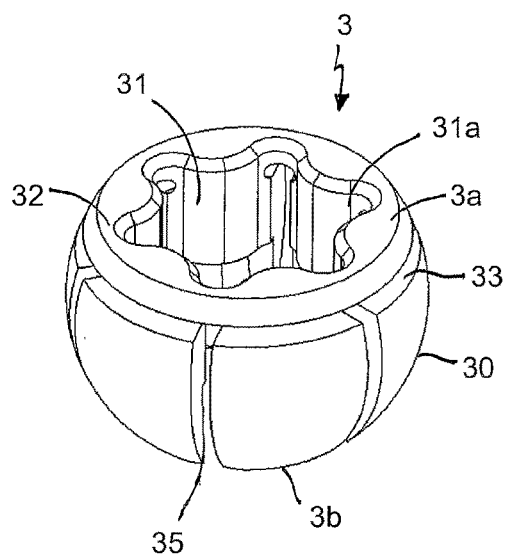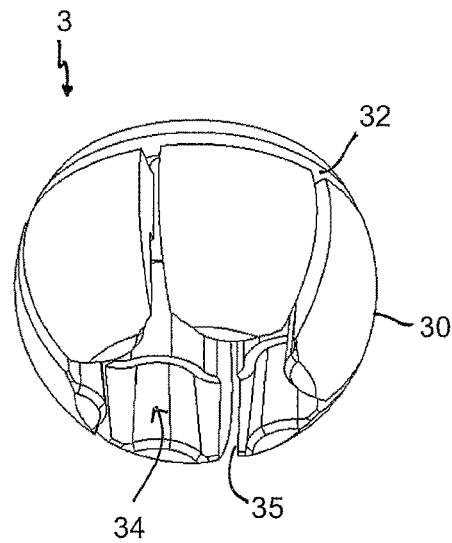
Fig.7　　　　　　　　Fig. 8
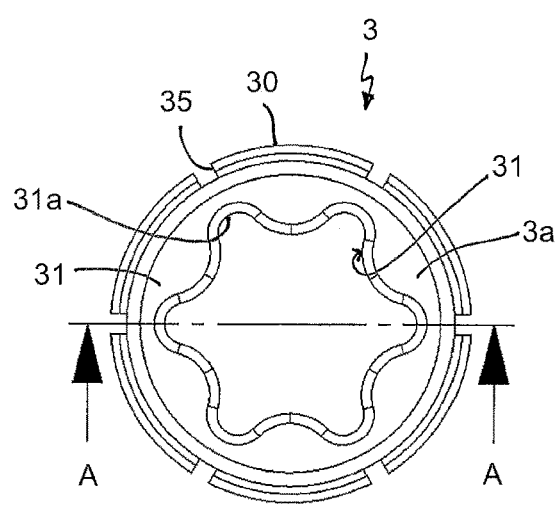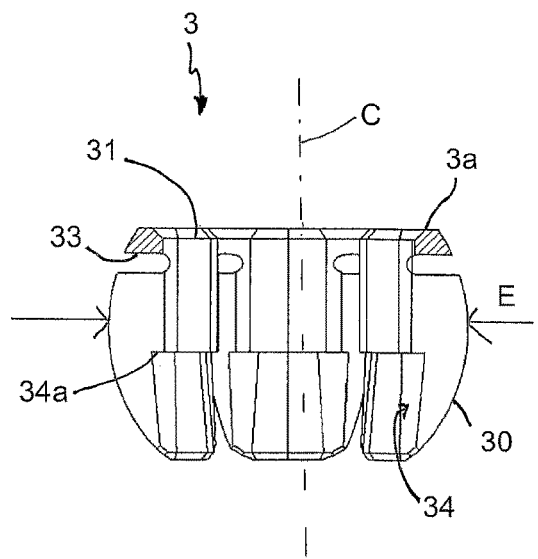
Fig. 9　　　　　　　　Fig. 10

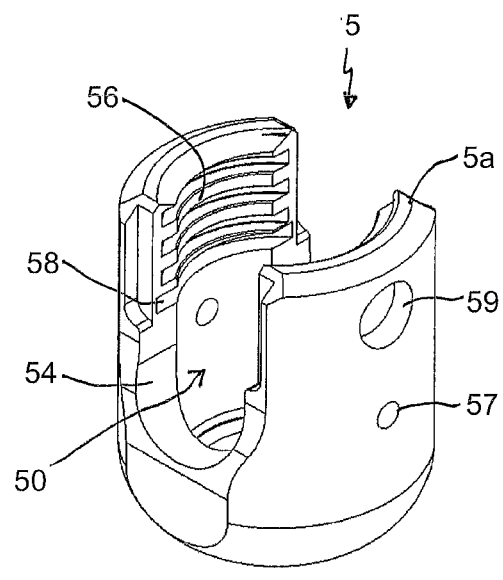
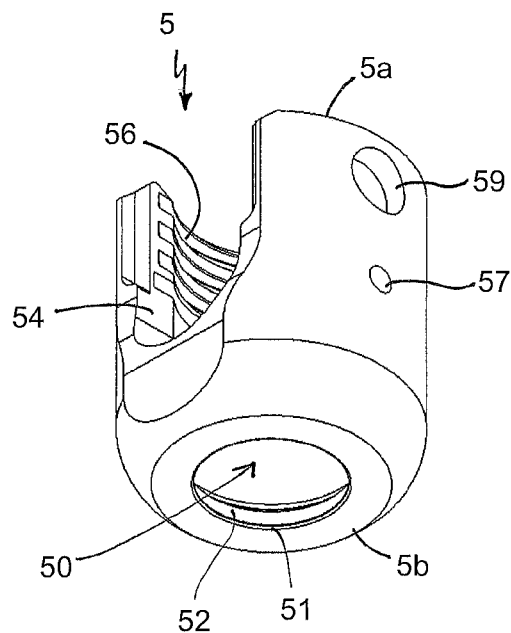
Fig. 11
Fig. 12
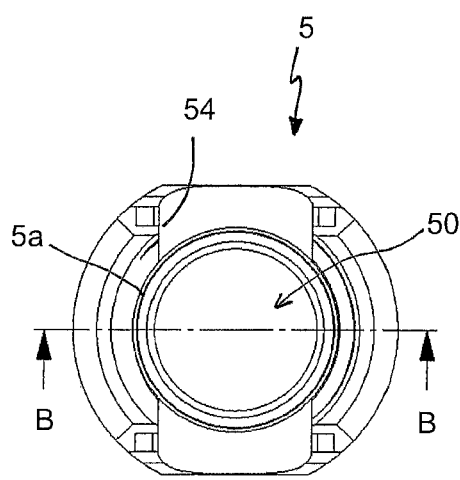
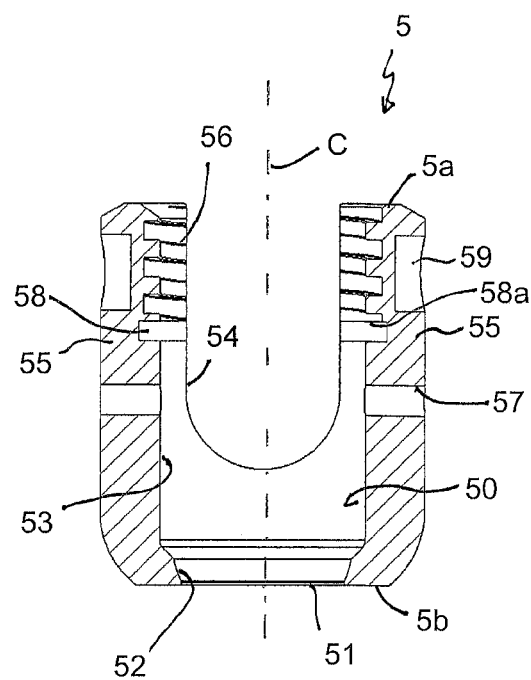
Fig. 13
Fig. 14

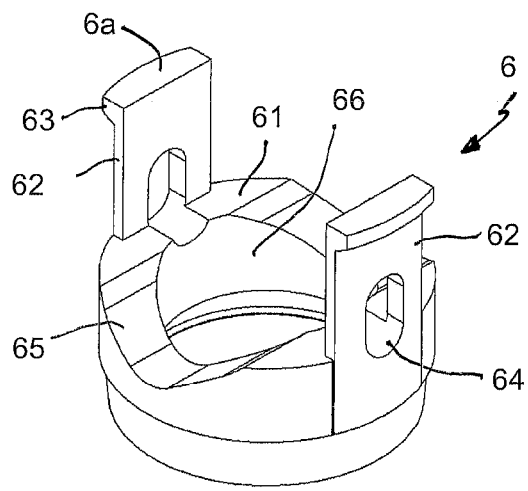
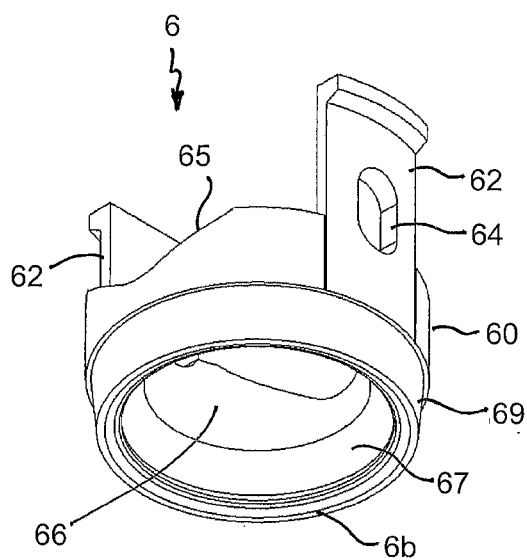
Fig. 15
Fig. 16
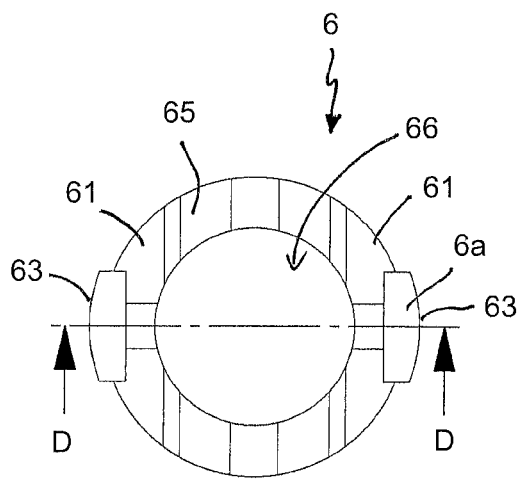
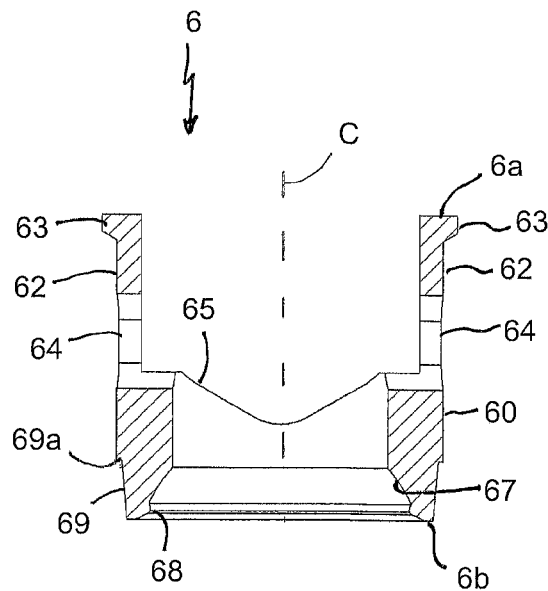
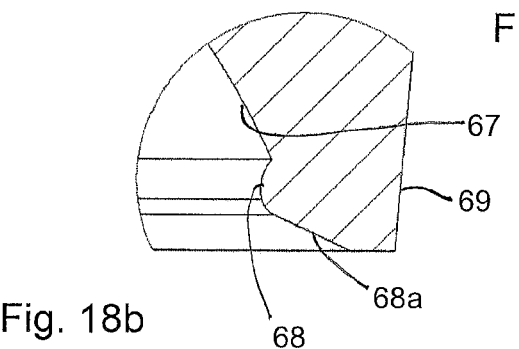
Fig. 17
Fig. 18a
Fig. 18b

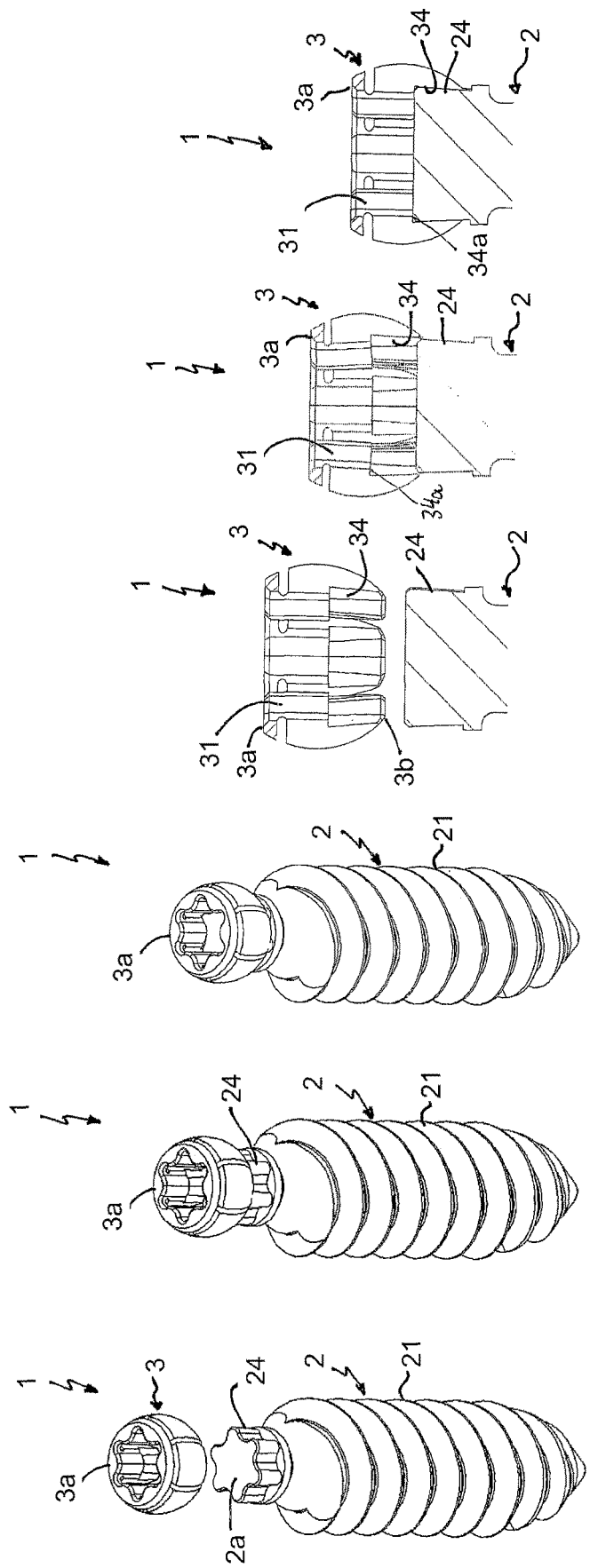

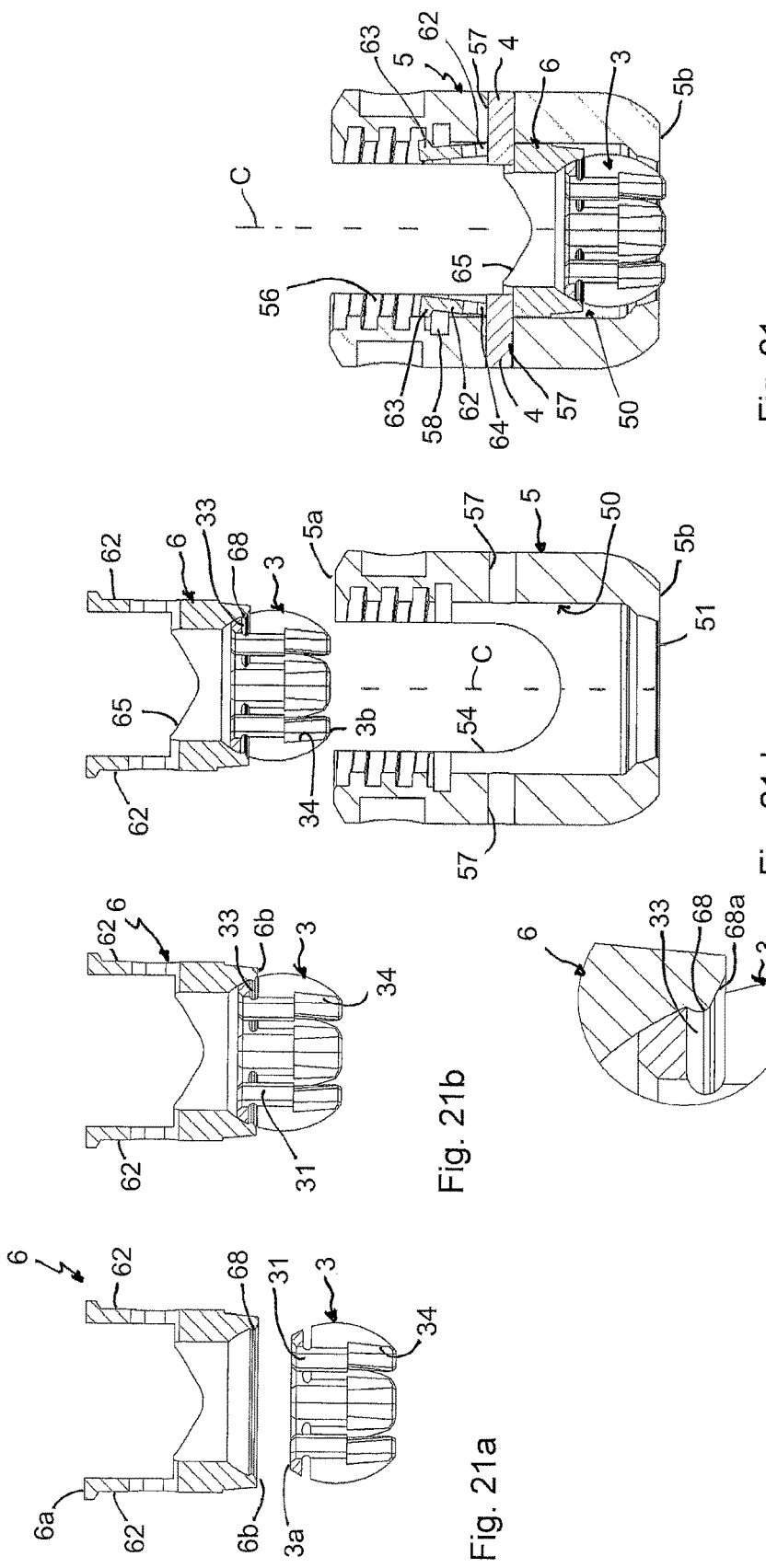

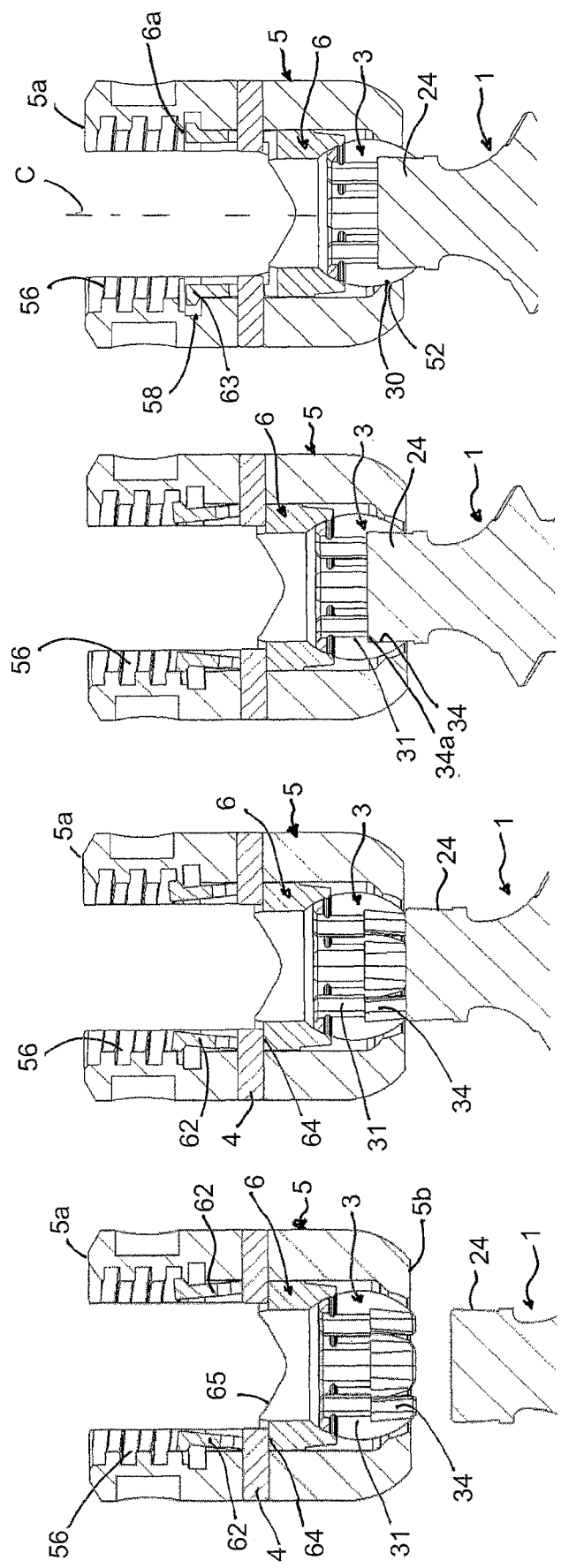

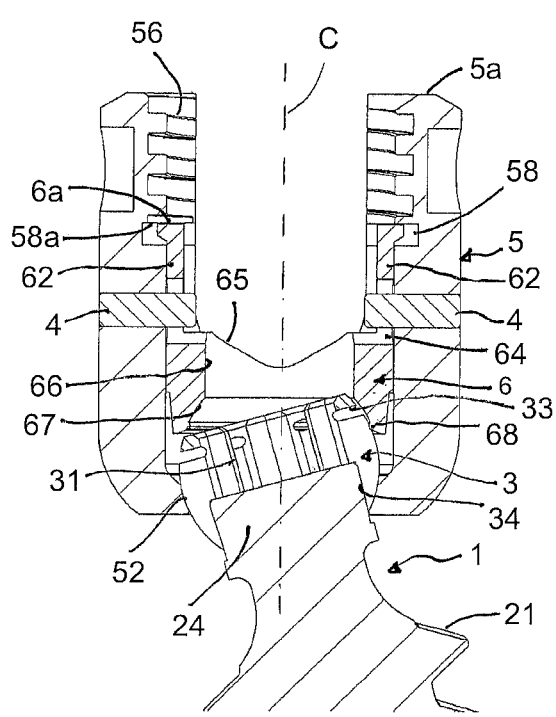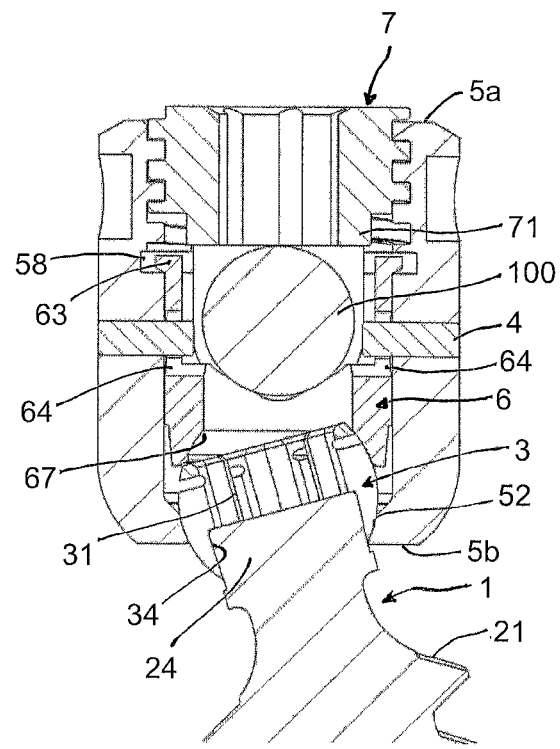
Fig. 23a  Fig. 23b
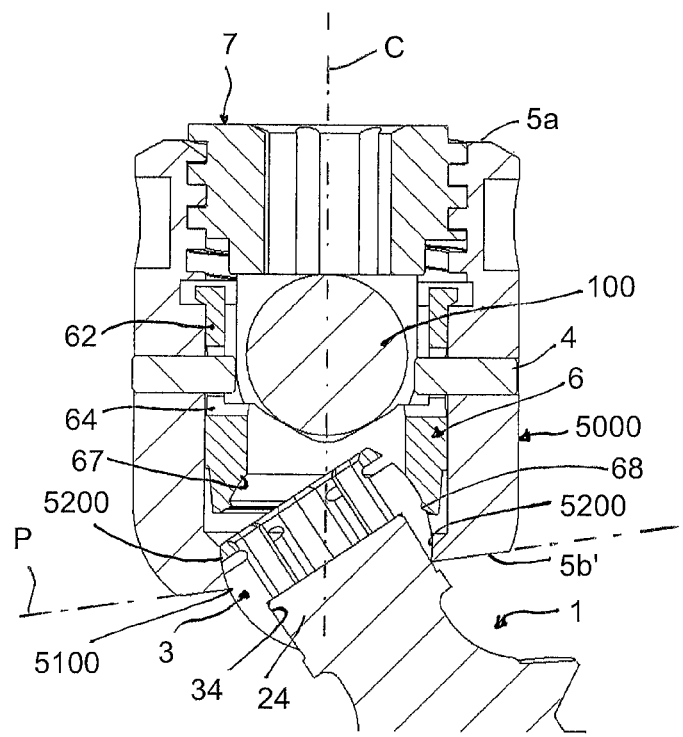
Fig. 24

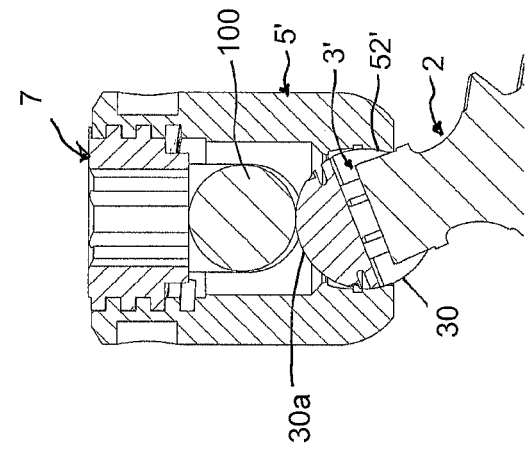
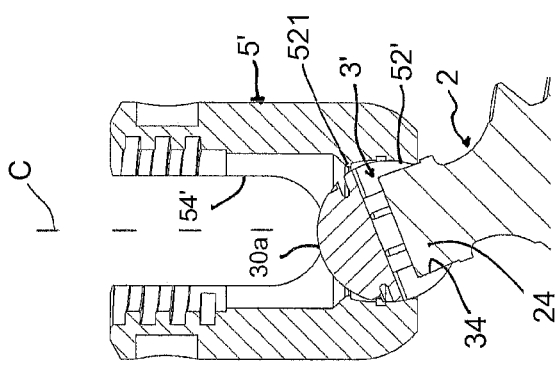
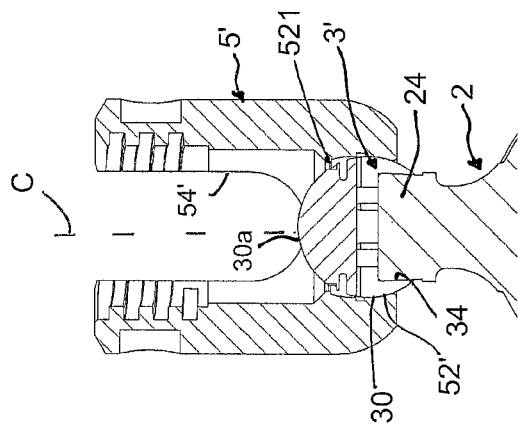
Fig. 37c
Fig. 37b
Fig. 37a

BONE ANCHORING DEVICE

CROSS-REFERENCE TO RELATED APPLICATION(S)

The present application is a continuation of U.S. patent application Ser. No. 17/394,748, filed Aug. 5, 2021, which claims priority to and the benefit of U.S. Provisional Patent Application No. 63/061,475, filed Aug. 5, 2020, the contents of which are hereby incorporated by reference in their entirety, and claims priority from European Patent Application EP 20 189 703.0, filed Aug. 5, 2020, the contents of which are hereby incorporated by reference in their entirety.

BACKGROUND

Field

The application relates to a bone anchoring device which is generally applicable in orthopedic and trauma surgery, and more particularly in spine surgery.

Description of Related Art

In spine surgery, one or several motion segments of the spine can be connected by a rod. The rod is anchored to the vertebrae using monoaxial or polyaxial bone anchoring devices. Such bone anchoring devices typically include a bone anchoring element to be anchored, for example, in the pedicle of a vertebra, wherein the bone anchoring element, in the case of a polyaxial device, is pivotably connected to a receiving part. The receiving part includes a recess for receiving the rod and a fixation member to fix or lock the construct.

U.S. Pat. No. 6,835,196 B2, for example, describes a polyaxial bone anchoring device with a screw having a threaded section and a head with a spherical segment-shape, and a receiving portion for connecting the screw to a rod. The thread section and the spherical segment-shaped head of the screw are separate parts. With such a device, it is possible during the application of the device to shorten the threaded section to a desired length before or after implanting, and then to connect the threaded section to the head and the receiving portion.

In US 2008/0132957 A1, a bone anchoring device is described that includes a shank to be anchored in a bone or vertebra, a head, and a receiving part for receiving the head for connecting the shank to a rod. The shank and the head are separate parts, and so in use of the bone anchoring device, an appropriate shank can be selected depending on the particular application and can be connected to the head for forming the bone anchoring device. In particular, shanks of different lengths can be provided in combination with the head.

US 2014/0277158 A1 describes bone anchor assemblies having a multi-component bone anchor that is configured to allow the shank of the bone anchor to be bottom-loaded into a receiver member. One bone anchor assembly has a shank with a distal threaded portion and a proximal head portion, a ball having a spherical exterior surface and a central lumen sized to receive the head portion of the shank, and a clip configured to be engaged between the head portion and the ball, such that the clip is utilized to lock the ball in engagement with the shank.

SUMMARY

It is an object of the invention to provide a bone anchoring device that permits an improved or alternative way of treating various orthopedic, in particular spinal, disorders, conditions, and/or diseases, and/or which opens up additional options for the application of the bone anchoring device.

According to an embodiment, the bone anchoring device includes an anchoring element having a shank for anchoring in bone and a head, the head having an exterior surface with a spherically-shaped section, wherein the shank and the head are separate parts configured to be connected to each other, and wherein the head has a drive structure for engagement with a drive tool.

The drive structure has an enlarged size compared to known anchoring elements with ball-shaped heads. This permits screwing or other advancement of the bone anchoring element into bone with an increased torque.

In a further development, a receiving part for receiving the head and for connecting the bone anchoring element to a rod is provided. Hence, the bone anchoring element and the receiving part may form a polyaxial bone anchoring device in which the shank can pivot at various angles relative to the receiving part and can be fixed at a particular angular position. A pressure element may be provided to transmit the force exerted by a fixation member to the head. Alternatively, the pressure can be transmitted via the rod directly onto the head.

The shank also includes an engagement portion for a drive tool. Therefore, it is possible to first insert the shank into the bone, and thereafter place the receiving part with the head assembled thereto onto the shank. Since the shank can be inserted without being coupled to the receiving part, the step of insertion may be better facilitated since the visibility and the available space at the implantation site are increased. If a correction of the insertion depth of the shank is necessary or the bone anchoring device has to be removed after head attachment, the drive structure of the head can be engaged and the required step can be effectively carried out.

In a specific embodiment, the shank may have a large outer diameter. The engagement portion of the shank may be also designed such as to permit the application of high torques.

Moreover, the bone anchoring device is robust and the receiving part with the inserted head is easily connectable to the shank.

In another way of use, the head and the shank can be assembled prior to coupling the head to the receiving part.

Various heads with different drive structures can be combined with a particular shank. Such different drive structures can be, for example, a torx-shaped drive structure or a mortorq® drive structure. In addition, a modular system can be provided where various heads can be combined with various shanks of different lengths, different diameters, different threads or bone engagement structures, or differing in one or more other properties.

In a further specific embodiment, the bone anchoring device includes a position indication structure that indicates a specific angular position of the head with shank relative to the receiving part, such as a zero angle position.

The bone anchoring device may also include a bone plate having a hole with a seat for the head of the bone anchoring element, and optionally, a locking member for locking the head in the hole.

BRIEF DESCRIPTION OF THE DRAWINGS

Further features and advantages of the invention will become apparent from the description of embodiments by means of the accompanying drawings. In the drawings:

FIG. 7 shows a perspective view from a top of the head of the bone anchoring device of FIGS. 1 to 3.

FIG. 8 shows a perspective view from a bottom of the head of FIG. 7.

FIG. 9 shows a top view of the head of FIGS. 7 and 8.

FIG. 10 shows a cross-sectional view of the head of FIGS. 7 to 9, the cross-section taken along line A-A in FIG. 9.

FIG. 11 shows a perspective view from a top of the receiving part of the bone anchoring device of FIGS. 1 to 3.

FIG. 12 shows a perspective view from a bottom of the receiving part of FIG. 11.

FIG. 13 shows a top view of the receiving part of FIGS. 11 and 12.

FIG. 14 shows a cross-sectional view of the receiving part of FIGS. 11 to 13, the cross-section taken along line B-B in FIG. 13.

FIG. 15 shows a perspective view from a top of a pressure member of the bone anchoring device of FIGS. 1 to 3.

FIG. 16 shows a perspective view from a bottom of the pressure member of FIG. 15.

FIG. 17 shows a top view of the pressure member of FIGS. 15 and 16.

FIG. 18a shows a cross-sectional view of the pressure member of FIGS. 15 to 17, the cross-section taken along line D-D in FIG. 17.

FIG. 18b shows an enlarged detail of FIG. 18a.

FIGS. 19a to 19c show perspective views from above of steps of mounting the head of the bone anchoring element to the shank.

FIGS. 20a to 20c show cross-sectional views of the steps shown in FIGS. 19a to 19c, respectively, wherein the cross-sections are taken in a plane including the shank axis and the central axis of the head.

FIGS. 21a to 21e show cross-sectional views of steps of assembling the head with a pressure member to the receiving part wherein FIG. 21c is an enlarged view of a detail of FIG. 21b.

FIGS. 22a to 22d show cross-sectional views of mounting the pre-assembled receiving part with head and pressure member to the shank.

FIG. 23a shows a cross-sectional view of the bone anchoring device of FIGS. 1 to 3, with the bone anchoring element in a pivoted position and the rod not inserted.

FIG. 23b shows a cross-sectional view of the polyaxial bone anchoring device in the pivoted position of FIG. 23a, with the rod and a fixation member inserted into the receiving part and with the pivot position locked.

FIG. 24 shows a cross-sectional view of a modified embodiment of the bone anchoring device with inserted rod and fixation member.

FIG. 35b shows an enlarged view of a detail of FIG. 35a.

FIGS. 37a to 37c show cross-sectional views of pivoting the bone anchoring element relative to the receiving part of the bone anchoring device of FIGS. 26 and 27, and locking the pivot position after insertion of the rod with the fixation member.

DETAILED DESCRIPTION

Figure 1:
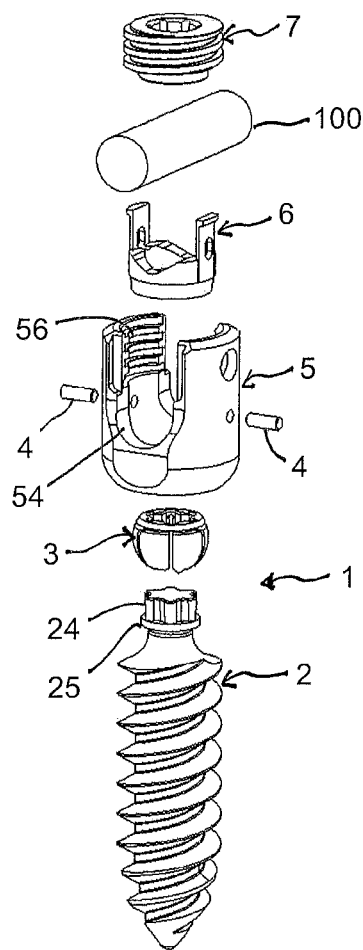
FIG. 1 shows a perspective exploded view of a first embodiment of a bone anchoring device.
Figure 2:
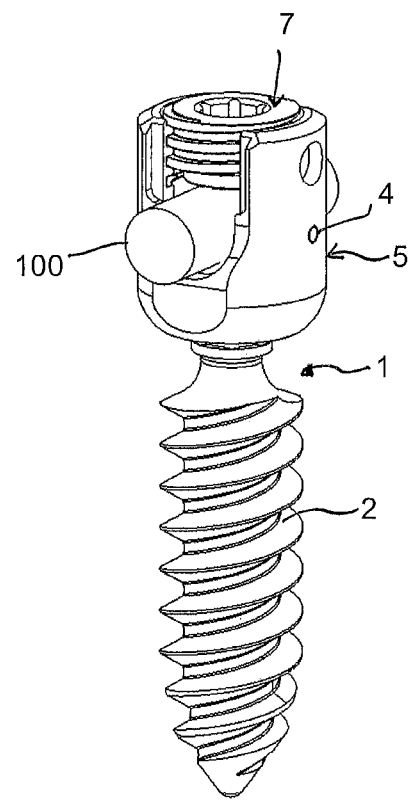
FIG. 2 shows a perspective view of the bone anchoring device of FIG. 1 in an assembled state.
Figure 3:
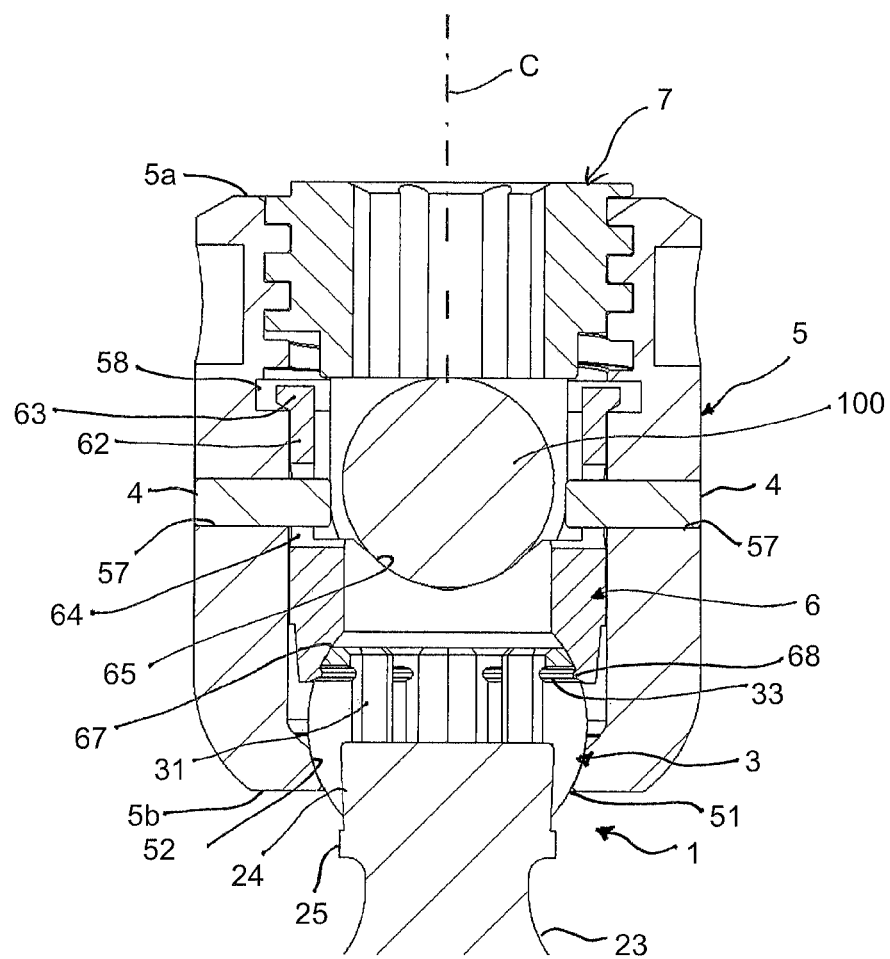
FIG. 3 shows a cross-sectional view of the polyaxial bone anchoring device of FIGS. 1 and 2, the cross-section taken in a plane extending through a center of a receiving part and a center of a head and including an axis of a shank.

Referring to FIGS. 1 to 3, a bone anchoring device according to a first embodiment includes a bone anchoring element 1 that has a shank 2 and a separate head 3. The bone anchoring element 1 is, via the head 3, pivotably coupled to a receiving part 5 that receives a pressure member 6 for transmitting pressure exerted by a fixation member 7 onto the head 3. A rod 100 is used to couple at least two bone anchoring devices together. The bone anchoring device is of the polyaxial type, which means that the anchoring element can assume various angular positions of the shank axis relative to the receiving part, and can be locked in each of these positions.

Figure 4:
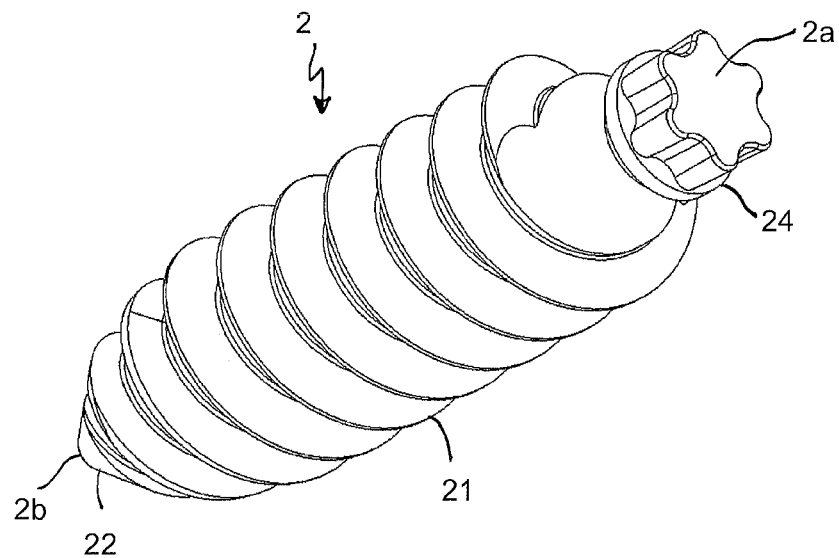
FIG. 4 shows a perspective view from a top of the shank of a bone anchoring element of the bone anchoring device of FIGS. 1 to 3.
Figure 5:
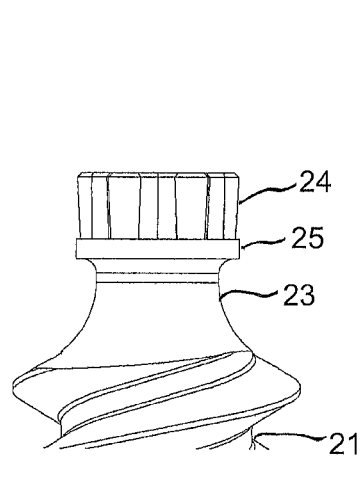
FIG. 5 shows a side-view of an upper portion of the shank of FIG. 4.
Figure 6:
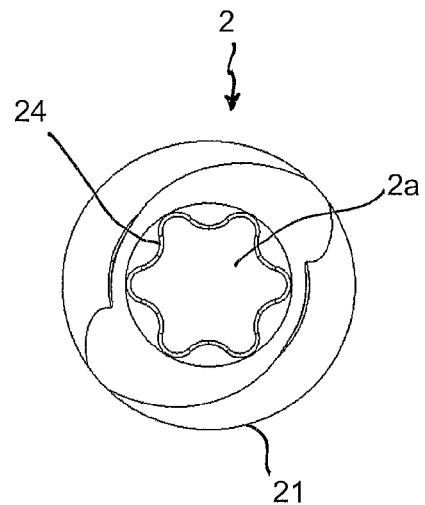
FIG. 6 shows a top view of the shank of FIGS. 4 and 5.

As depicted in greater detail in FIGS. 4 to 6, the shank 2 has a first end 2a and an opposite end 2b, and a bone thread portion 21 on at least a portion of its length. The bone thread is configured to engage bone. In the embodiment shown, the bone thread portion 21 extends over almost an entire length of the shank from a tip 22 at the second end 2b up to a neck portion 23. At the first end 2a, an engagement portion 24 is formed, which has an outer surface with a structure that is configured to be engaged by a drive tool, such as a star-like structure, a torx-like structure, or a polygonal outer contour. A maximum outer width of the engagement portion 24 may be smaller than a maximum outer diameter of the bone thread portion 21. Hence, in this embodiment, the shank has a relatively large diameter. More specifically, a maximum outer diameter of the bone thread portion 21 may be greater than a maximum outer diameter of the head 3. The engagement portion 24 may be limited by a substantially cylindrical portion 25 that forms an annular ring which may serve as a stop for the drive tool.

Referring to FIGS. 7 to 10, the head 3 has a first end 3a and an opposite second end 3b, and a spherical segment-shaped outer surface 30 between the first end and the second end. The spherical shape is such that the outer surface 30 includes the greatest diameter E of the sphere in a direction perpendicular to the central axis C which coincides with the shank axis when the head 3 is mounted to the shank 2. Moreover, the distance from the greatest diameter E to the first end 3a may be smaller than the distance between the greatest diameter E and the second end 3b. More specifically, the axial height of upper portion of the head 3, i.e., between the greatest diameter E and the first end 3a, is as small as possible to still permit pivoting on the one hand, and to provide sufficiently large space at the first end for a drive structure 31 on the other hand. The drive structure 31 in this embodiment includes a recess extending in the axial direction from the first end 3a to a distance beyond the greatest diameter E towards the second end 3b. The recess has an inner contour that has a star-like shape, more specifically, a torx-shape that has six radially extending longitudinal grooves 31a that have rounded ends and are arranged at regular distances. The distance of the outermost end of the grooves 31a in the radial direction seen from the central axis C is such that the drive structure 31 extends over substantially the entire surface at the first end 3a, leaving only a small rim 32 that extends to the outer spherical segment-shaped surface 30. With this design, the drive structure 31 permits a more robust engagement of the head and the ability to apply an increased torque to the shank 2.

At a distance from the first end 3a, a circumferential groove 33 is formed in the outer spherical segment-shaped surface 30. The groove 33 may extend fully around the central axis C. Moreover, the groove 33 may be located closer to the first end 3a than to the axial position of the greatest diameter E. The depth of the groove 33 in the radial direction may be such that the groove extends into the grooves 31a of the drive structure 31, as depicted in FIGS. 7 and 10.

At the second end 3b, a counterpart engagement portion 34 is formed as a recess which is configured to receive the engagement portion 24 of the shank 2. In other words, the inner contour of the counterpart engagement portion 34 substantially matches the outer contour of the engagement portion 24 of the shank. Also, the depth of the recess forming the counterpart engagement portion 34 corresponds substantially to the axial length of the engagement portion 24. In addition, the recess has a slightly tapering inner wall that tapers and narrows towards the second end 3b. The drive structure 31 and the counterpart engagement portion may be in communication with each other. A shoulder 34a between the recess and the drive structure 31 forms a stop for the insertion of the engagement portion 24 of the shank.

The head 3 is at least partly flexible in a region adjacent the second end 3b. This is achieved by means of a plurality of longitudinal slits 35 that are open to the second end 3b and that extend at least up to the greatest diameter E, preferably up to and into the circumferential groove 33. The number and width of the slits 35 is selected such that the head 3 exhibits in the lower portion adjacent to the second end 3b sufficient flexibility to permit insertion of the engagement portion 24 in a snap-on manner and to hold the engagement portion 24 in the recess. The tapered inner wall of the recess permits tight engagement of the engagement portion 24.

Referring to FIGS. 11 to 14, the receiving part 5 will be described in greater detail. The outer shape of the receiving part 5 may be substantially cylindrical. The receiving part has a first end or top end 5a, a second end or bottom end 5b, and a passage 50 extending completely through the receiving part 5 from the first end 5a to the second end 5b. The central longitudinal axis C coincides with the central longitudinal axis C of the head 3 when the head 3 is at a zero position in the receiving part 5. An opening 51 at the second end 5b may have a size such that at least a portion of the lower end of the head 3 can extend therethrough. Adjacent to the second end 5b, the passage 50 forms an accommodation space for at least a portion of the head 3. More specifically, adjacent to the second end 5b, a seat 52 is formed for the head 3. The seat 52 may have a hollow spherical segment shape that matches the spherical segment shape of the head 3. When the head 3 is accommodated in the lower portion of the receiving part adjacent to the second end 5b, the head is supported in the seat 52 and configured to pivot therein like a ball and socket joint. Any other shape of the seat that provides this function can also be implemented.

Adjacent to the seat 52, the passage 50 widens into a main section 53 that has a substantially constant inner diameter. Starting from the first end 5a, a substantially U-shaped recess 54 is formed, resulting in two free legs 55. The substantially U-shaped recess 54 forms a channel which is configured to receive the rod 100 therein. In addition, adjacent to the first end 5a, an inner thread 56 is formed on the legs 55 which is configured to cooperate with a fixation member 7, for example a set screw. The inner thread may be of any thread type, preferably a thread type that reduces splaying of the legs 55, such as, for example, a square thread or flat thread. At the center of the legs 55 in the circumferential direction, transverse through-holes 57 are formed in each leg, respectively. The through-holes 57 may be at an axial position above a bottom of the substantially U-shaped recess 54 and below the threaded portion 56. The through-holes 57 serve for receiving pins 4 that are configured to extend completely through the through-holes 57 into the passage 50. At the lowermost end of the inner thread 56, a circumferential groove 58 or undercut is formed on each leg 55 that provides, with its upper surface 58a, an abutment for a portion of the pressure member 6. Additional tool engagement recesses 59 may be provided in the outer surface of the legs 55, respectively.

Referring to FIGS. 15 to 18b, the pressure member 6 has a first end 6a and an opposite second end 6b, and is configured to be arranged in the receiving part 5 such that the second end 6b faces towards the second end 5b of the receiving part. An upper portion 60 of the pressure member 6 is substantially cylindrical such that it fits into the cylindrical portion 53 of the passage 50 in the receiving part and can move therein in an axial direction to some extent. Hence the cylinder axis C is coincident with the central longitudinal axis of the receiving part 5 when the pressure member 6 is arranged in the receiving part 5. Two opposite legs 62 offset by 180° stand upright away from an upper surface 61 of the cylindrical portion 60. The legs 62 may have flat inner walls facing each other and cylindrical outer walls corresponding to the shape of the cylindrical portion 60. At the first end 6a, each leg includes an outwardly protruding rim 63 that extends beyond the outer surface of the cylindrical section 60 in a radial direction. The legs 62 have a length and thickness such that they are flexible at least partially in the region of their free end and can be compressed towards each other and resiliently move back to their straight position. The upper surface of the protruding rim 63 forms the first end 6a of the pressure member 6. In each leg 62, an axial elongate hole 64 is provided that serves for receiving a portion of the pin 4.

The pressure member 6 is further configured to support the rod 100 and therefore has a recess 65 that extends perpendicular to the cylinder axis C of the cylindrical portion 60. The recess 65 forms a support surface for an inserted rod 100. The cross-section of the recess 65 may be substantially V-shaped, as can be seen in particular in FIG. 18a, preferably with a rounded bottom. By means of this, rods of different diameters can be safely supported so that they are substantially prevented from moving in a direction transverse to the rod axis. A bore 66 that is coaxial with the cylinder axis of the cylindrical portion 60 extends from the upper surface 61 of the cylindrical portion to the second end 6b and provides access to the head 3 for a drive tool. As a consequence, the inner diameter of the bore 66 is at least as large as the greatest width of the recess with the drive structure 31 on the head, so that a drive tool can engage the drive structure 31 when the drive tool extends through the bore 66. At a distance from the second end 6b a substantially spherical segment-shaped recess 67 is formed, the shape of which matches the outer spherical shape of the head 3. A height of the spherical portion 67 in the axial direction is such that when the head 3 is mounted to the pressure member 6 and to the receiving part 5 and rests in the seat 52 of the receiving part in a zero angle position of the shank 2, the upper portion of the head 3 between the groove 33 and the first end 3a lies within the spherical recess 67. Moreover, the spherical recess 67 and the seat 52 together form a spherical pivot support for the head 3, as can be seen in particular in FIGS. 23a to 24.

Between the spherical recess 67 and the second end, the pressure member 6 includes an inner circumferentially extending protrusion 68 that protrudes inwardly towards the central axis C. The protrusion 68 is at a position corresponding to and has a shape adapted to the position and shape of the circumferential groove 33 on the head 3 when the head 3 extends into the spherical recess 67 of the pressure member. To enable easier engagement with and disengagement from the groove 33, the protrusion may be rounded. Moreover, when the head 3 is supported in the seat 52 of the receiving part 5, the protrusion 68 is configured to engage the groove 33. As the groove 33 as well as the protrusion 68 extend perpendicular to the central axis C, the engagement is achieved when the head 3 is at a zero angle position of the shank relative to the receiving part 5 (i.e., when central axes of the shank and the receiving part are coaxial). The engagement can produce an audible or tactile feedback. Therefore, the groove and the protrusion form a position indication structure configured to indicate a specific position of the shank relative to the receiving part. In the specific example, the specific position is the zero position where the shank 2 is coaxial with the receiving part 5. Between the protrusion 68 and the second end 6b, an outwardly tapering section 68a may be provided that facilitates insertion of the head 3 into the pressure member 6. The outwardly tapering section 68a may form a ramp for the head 3 when the head pivots so that the protrusion 38 can move easier move out of the groove 33.

The outer surface 69 between the second end and up to a distance beyond the spherical section 67 may be slightly tapered and narrows towards the second end 6b, whereby a step 69a may be formed. By means of this, a wall thickness is slightly reduced so that the protrusion 68 can snap into the groove 33 more easily.

The parts and portions of the bone anchoring device and of the rod may be made of any material, preferably however, of titanium or stainless steel, or of any bio-compatible metal or metal alloy or plastic material. For a bio-compatible alloy, a NiTi alloy, for example Nitinol, may be used. Other materials that can be used are magnesium or magnesium alloys. Bio-compatible plastic materials that can be used may be, for example, polyether ether ketone (PEEK) or poly-L-lactide acid (PLLA). The various parts can be made of the same or of different materials from one another.

Mounting of the head to the shank will be described, referring to FIGS. 19a to 20c. It shall be noted that the bone anchoring element can be used in many applications, so that the assembled bone anchoring element can be inserted as one piece in, for example, receiving parts of polyaxial bone anchors or bone plates with locking screws. As shown in the figures, first, the head 3 is oriented such that the counterpart engagement portion 34 of the head 3 and the engagement portion 24 of the shank 2 are facing each other and the recesses are rotationally aligned (FIGS. 19a and 20a). Then, the head 3 is pressed onto the engagement portion 24 of the shank 2 so that the lower portion of the head 3 in the region of the recess 34 is spread apart to let the engagement portion 24 enter (FIGS. 19b and 20b). Then, the engagement portion 24 moves within the recess until it abuts with the end surface 2a at the shoulder 34a of the recess 34a and the counterpart engagement portion 34 closes around the engagement portion 24. The head 3 is now rotationally fixed due to the form-fit engagement of the engagement portions of the shank and the head. In the axial direction, the shank 2 may be held to some extent by friction within the recess.

Steps of assembling the receiving part 5 with the pressure member 6 and the head 3 are shown in FIGS. 21a to 21e. As shown in FIGS. 21a to 21c, the head 3 is inserted with the leading first end 3a into the pressure member 6 from the second end 6b thereof, until the protrusion 68 of the pressure member 6 engages the groove 33 of the head 3. Thus, the protrusion 68 and the groove 33 provide a holding structure for holding the pressure member 6 and the head 3 together. Once assembled, the pressure member 6 and the head 3 are inserted from the first end 5a into the receiving part 5, with the second end 3b of the head 3 facing towards the opening 51. The rod recesses 54 and 65 of the receiving part 5 and the pressure member 6 are aligned.

During insertion of the pressure member 6 with the head 3 assembled therewith, the legs 62 of the pressure member 6 are slightly compressed towards each other as the outer rim 63 abuts against the crests of the inner thread 56 of the receiving part 5. When the outer rim 63 is at the thread crest immediately above the groove 58, the elongate hole 64 overlaps the through hole 57 and the pins 4 can be inserted, as shown in FIG. 21e. The pins 4 also form a securing structure against rotation of the pressure member in the receiving part. In this position, the head 3 is in the accommodation space and not yet in the seat 52. This is the insertion position which is defined at an uppermost position of the pressure member 6, in which the pressure member 6 abuts with the lower end of the elongate hole 64 against a stop provided by the pins 4, respectively. Between the outer spherical surface 30 of the head 3 and the seat, there is still enough space to allow for spreading of the lower portion of the head 3 to permit the insertion of the engagement portion 24 of the shank 2. the head may protrude slightly out of the opening 51.

Referring to FIGS. 22a to 22d, the mounting of the pre-assembled receiving part, with pressure member 6 and head 3, to the shank 2 is shown. In FIG. 22a the engagement portion 24 of the shank 2 and the receiving part 5 are rotationally aligned with respect to each other so that the engagement portion 24 of the shank 2 can be inserted into the recess of the counterpart engagement portion 34 of the head 3 (FIG. 22b). As the lower portion of the head 3 is flexible, the lower portion can spread to permit the engagement portion 24 to enter. The pins 4 prevent upward movement of the pressure member 6 during the insertion step. FIG. 22c shows the step in which the engagement portion 24 has been fully inserted into the recess of the counterpart engagement portion 34 and abuts against the shoulder 34a.

Finally, as shown in FIG. 22d, the pressure member 6 is moved towards the second end 5b of the receiving part so that the head 3 comes into contact with the seat 52 of the receiving part and is supported there. Simultaneously, the outer rim 63 snaps into the groove 58. The upper surface 58a of the groove provides an abutment for the upper surface 6a of the pressure member at the legs 62 so that the head 3 is held in the seat 52. The spherical recess 67 of the pressure member contacts a portion of the upper part of the head 3, so that the head 3 can be held by friction in this position. Depending on the dimensions of the parts, this friction holding of the head 3 can be strong or weak. Preferably, the frictional force can be manually overcome by pivoting the receiving part 5 relative to the head 3 and the shank 2. Simultaneously, the lower portion of the head 3 is compressed in the seat 52 so that the head firmly holds the engagement portion 24 of the shank.

As depicted in FIG. 23a, when the receiving part 5 is pivoted relative to the shank 2, the protrusion 68 moves out of the groove 33 and allows the head 3 to pivot in the spherical seat 52 while also being held by a portion of the spherical recess 67. When the pivot position of the shank 2 relative to the receiving part 5 is changed to the zero angle position, i.e., the position in which the shank axis is coaxial with the central longitudinal axis C of the receiving part, the protrusion 68 snaps into the groove 33, thereby producing an audible or tactile feedback which indicates that the defined position, in this case the zero angle position, is reached.

Once a desired angular position has been found or reached, the rod 100 is inserted until it rests on the support surface 65 of the pressure member 6. The fixation member 7 is inserted between the legs 55 of the receiving part and tightened so that the fixation member exerts pressure onto the rod and via the pressure member onto the head to lock the angular position of the head relative to the receiving part, as shown in FIG. 23b. The fixation member may have a protrusion 71 for pressing on the rod while the legs 62 are not in contact with the fixation member.

In clinical use, at least two bone anchoring devices are inserted into bone and connected through a rod. The bone anchoring device according to embodiments of the invention can be used in a number of different ways. For example, the shank 2 may already be inserted into bone and the pre-assembled receiving part 5 with pressure member 6 and head 3 may be mounted onto the engagement portion of the shank in-situ. In another option, in the configuration in which the head 3 and the pressure member 6 are pre-assembled with the receiving part 5, the head can be mounted to the shank 2 prior to inserting the shank 2 into bone. Both options are useful, for example, when the shank is a large diameter shank which cannot pass through the opening 51. If a shank is used that has a smaller outer diameter that can be guided through the opening 51, the head 3 and the shank 2 can also be pre-assembled as shown in FIGS. 19a to 20c and guided through the receiving part 5 from the top end thereof, until the head 3 rests in the seat 52. Thereafter, the pressure member 6 can be inserted and secured with the pins 4.

It shall be noted that various shanks can be used and connected to the head and the receiving part so that the bone anchoring device can provide a modular system which allows the use of many different shanks combined with the head and the receiving part.

When the shank is inserted into bone prior to mounting the receiving part with pressure member and head thereon, the engagement portion 24 of the shank 2 provides the drive structure for engagement with a drive tool. Because the engagement portion is relatively large, higher torques can be applied. On the other hand, once the bone anchoring device has been fully assembled as shown in FIG. 22d, the drive structure 31 of the head 3 is also relatively large, so that higher torques can be applied through the head 3. This can be useful for inserting the bone anchoring device in the configuration of FIG. 22d into the bone, for performing corrections on the position of the shank in the bone, or when the bone anchoring device has to be removed completely.

FIG. 24 shows a modified embodiment of the bone anchoring device which differs from the first embodiment shown in FIGS. 1 to 23b in that it permits pivoting of the bone anchoring element relative to the receiving part at a larger maximum angle to one side compared to the opposite side. The receiving part 5000 has a lower end 5b' in which a plane P defined by the opening 5100 extends in an inclined manner relative to the central axis C. This can be manufactured, for example, by cutting an end portion of the receiving part at an angle. The seat 5200 for the head is increased in the axial direction so that the seat provides enough support surface for the head 3 in the region with the enlarged pivot angle. As illustrated in FIG. 24, the bone anchoring element 1 is pivoted to one side at a larger maximum angle which may be limited by an abutment of a portion of the shank at the lower end 5b' of the receiving part. It shall be noted that other geometries of the receiving part and/or the shank may be provided that permit the shank to pivot at a greater maximum angle in one or more directions than in other directions.

Figure 25:
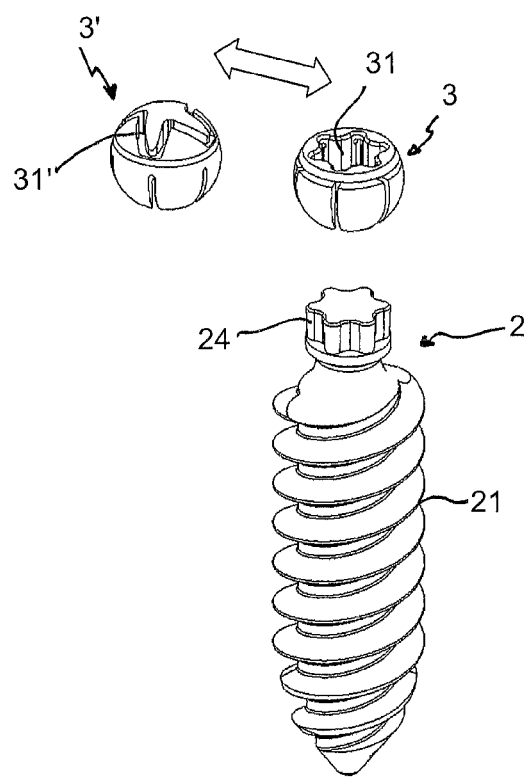
FIG. 25 shows a perspective view of an embodiment of a system including the shank and two exchangeable heads for forming a bone anchoring element of the bone anchoring device.
Figure 26:
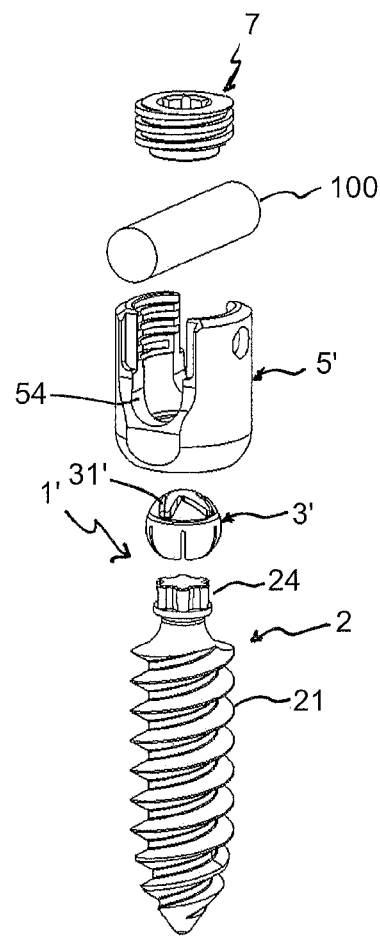
FIG. 26 shows a perspective exploded view of a bone anchoring device according to a second embodiment.
Figure 27:
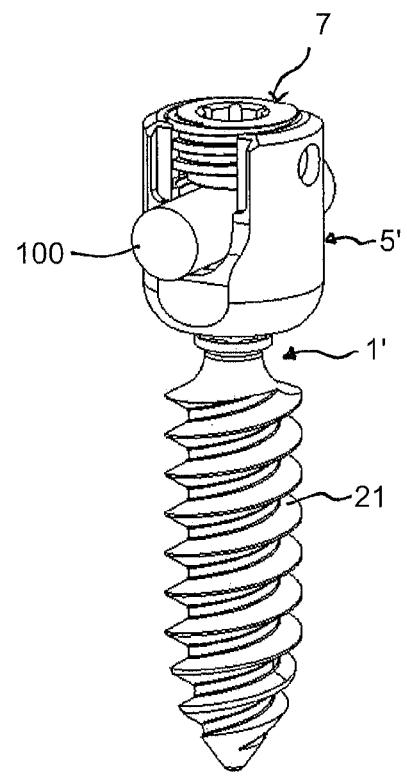
FIG. 27 shows a perspective view of the bone anchoring device of FIG. 26 in an assembled state.
Figure 28:
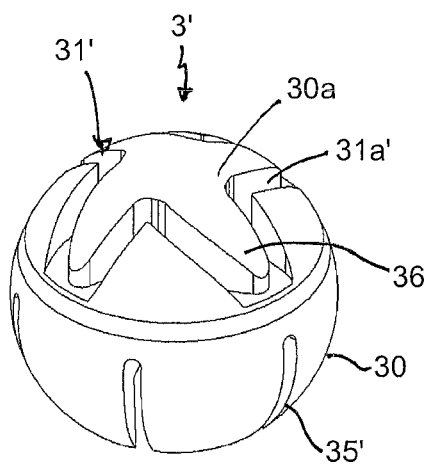
FIG. 28 shows a perspective view from a top of a head of the bone anchoring device of FIGS. 26 and 27.
Figure 29:
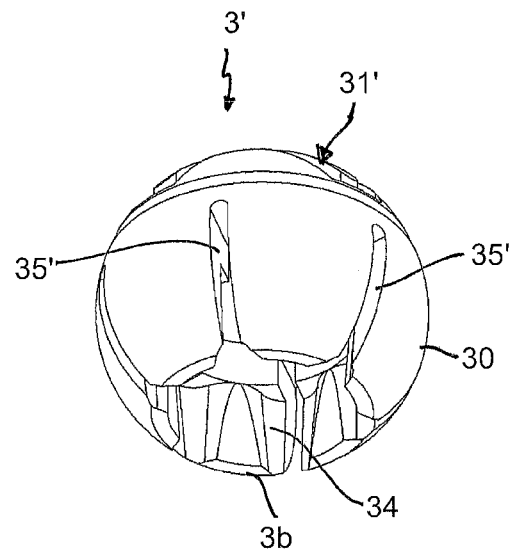
FIG. 29 shows a perspective view from a bottom of the head of FIG. 28.
Figure 30:
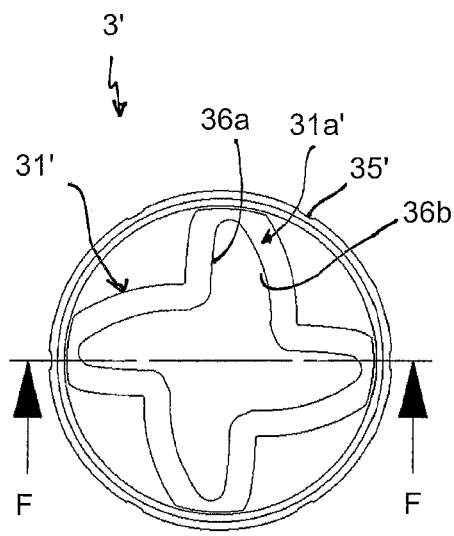
FIG. 30 shows a top view of the head of FIGS. 28 and 29.
Figure 31:
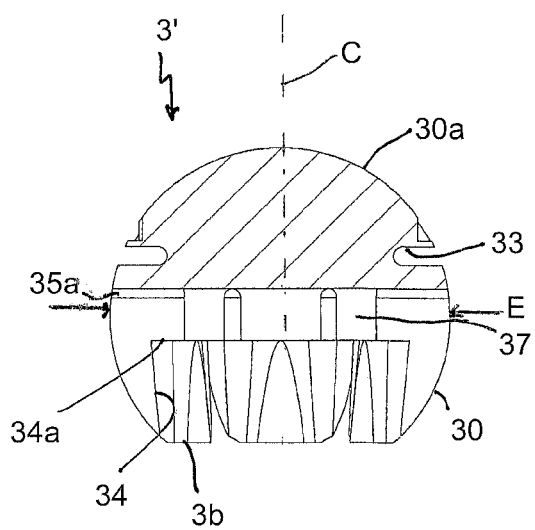
FIG. 31 shows a cross-sectional view of the head of FIGS. 28 to 30, the cross-section taken along line F-F in FIG. 30.
Figure 32:
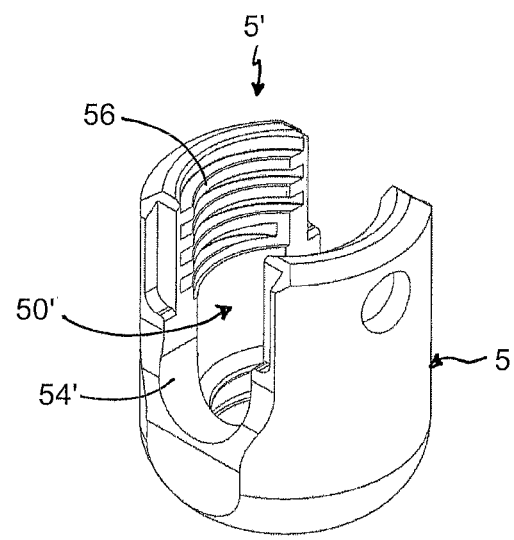
FIG. 32 shows a perspective view from a top of a receiving part of the bone anchoring device of FIGS. 26 and 27.
Figure 33:
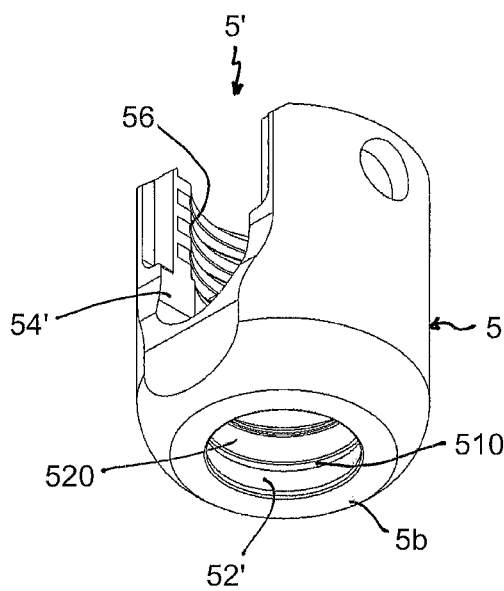
FIG. 33 shows a perspective view from a bottom of the receiving part of FIG. 32.
Figure 34:
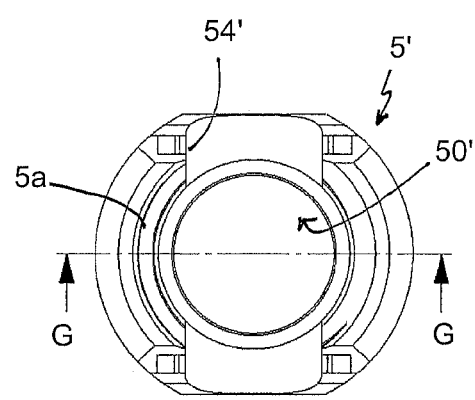
FIG. 34 shows a top view of the receiving part of FIGS. 32 and 33.
Figure 35A:
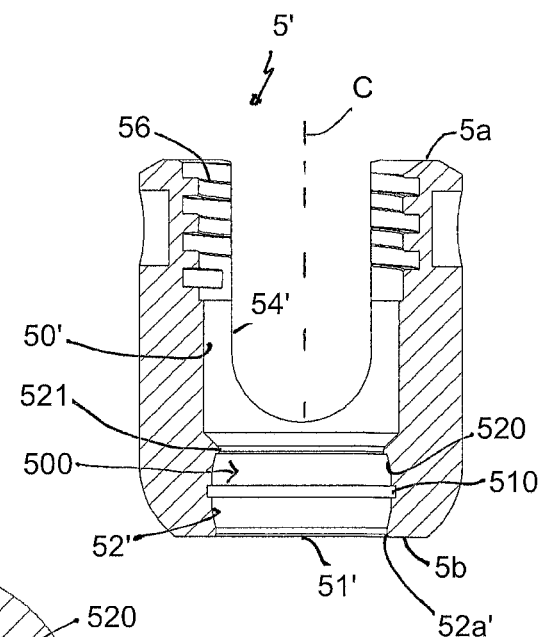
FIG. 35a shows a cross-sectional view of the receiving part of FIGS. 32 to 34, the cross-section taken along line G-G in FIG. 34.
Figure 35B:
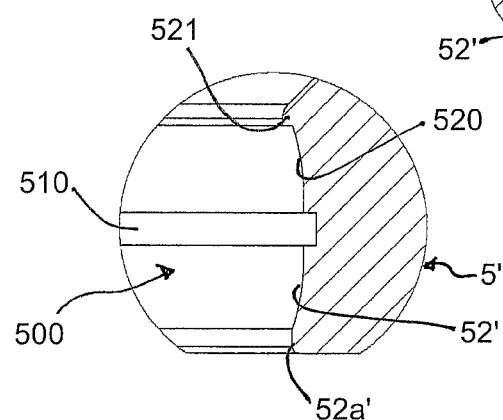

A modular system can also be provided using different heads. As shown in FIG. 25, besides the head 3 as described above, another head 3' with a different drive structure can be combined with the shank 2. Hence, since the bone anchoring device opens various options of assembly and use, such options can be further enlarged by adding various heads with different properties, such as different drive structures, different materials, different flexibility, or other properties to be selectively combined with a shank.

The head 3' shown in FIG. 25 includes a drive structure 31' that is identical or similar to a mortorq® drive. Depending on the size of the drive structure 31', the head 3' can be used with the receiving part 5 and the pressure member 6 of the first embodiment in an exchangeable manner with the head 3.

The head 3' can also be part of a second embodiment of the bone anchoring device as shown in FIGS. 26 to 37c. Identical or similar parts and portions thereof are marked with the same reference numerals as in the first embodiment, and the descriptions thereof will not be repeated. The bone anchoring device includes a bone anchoring element 1' having the shank 2 as in the first embodiment or another shank, the head 3', and a receiving part 5'. This embodiment differs from the first embodiment in that the pressure member is not needed, so that the rod 100 can transmit the pressure exerted by the fixation member 7 directly onto the head 3'.

Referring to FIGS. 28 to 31, the head 3' is substantially solid in the upper portion and has an outer spherical surface 30a in the upper portion, with a radius that may be identical to the radius of the spherical outer surface 30 of the lower portion. In other words, the head 3' may have a substantially outer fully spherical surface except at the second end 3b, which may be substantially flat. In the upper surface 30a, the drive structure 31' is provided in the form of a groove 31a' that forms wings or lobes that emanate from a center which is coincident with the apex, i.e., the highest point on the spherical upper surface 30a in a curved manner. In greater detail, the groove 31a forms four wings 36 that are all curved towards the same side and have the same shape and size and a regular distance. Such a design is known as a mortorq® drive. Each wing of the groove includes a substantially straight or slightly oblique section 36a and a rounded section 36b, wherein the two sections are connected at the tip of the wing. The groove 31a' is open at the tip of the wings 36 towards the outer surface, as can be seen in particular in FIG. 28. This kind of drive structure is configured to transmit higher torques compared to various other drive structure. The groove 33 and the engagement portion 34 are the same as in the first embodiment. To enhance flexibility of the head 3', there may be a second, central recess 37 following the engagement recess 34 in the direction towards the spherical upper surface 30a which has a smaller inner diameter so that the shoulder 34a is formed. The slits 35' may end at a distance from the groove 33 and may continue into inner transverse slits 35a, also for increased flexibility. However, the slits 35 and the central recess 37 cover the region with the greatest outer diameter E of the head 3, so that the greatest diameter of the head 3' is slightly compressible towards the central axis C.

Referring to FIGS. 32 to 35b, the receiving part 5' has an accommodation space 500 for the head 3' in which the head 3' can assume an insertion position and a final position for pivoting. To achieve this, the accommodation space 500 has near the second end 5b a lower seat 52', more specifically a hollow spherical segment-shaped portion with a radius matching the radius of the lower outer spherical surface 30 of the head 3'. The height of the lower spherical seat 52' is such that the lower seat 52' extends slightly over the greatest outer diameter E of the head 3' when the head 3' rests with the spherical outer surface 30 in the lower seat 52'. By means of this, the head 3' is held in a pivot position by friction within the lower seat 52'. This prevents the head 3' from being inadvertently kicked out of the lower seat 52' when it is in the pivot position and the rod and fixation member are not yet inserted and fixed. The lower seat 52' may widen with a small section 52a' towards the second end 5b to facilitate insertion of the head 3'. The opening 51' at the second end 5b has a size such that the head 3' can be introduced from the second end by compressing the head slightly. In addition, the accommodation space 500 has an upper seat 520 that is separated from the lower seat 52' by a circumferential inner groove 510 which has a diameter greater than the largest diameter E of the head 3'. The inner groove 510 allows the head 3' to pass from the upper seat 520 into the pivot position in the lower seat 52'. The upper seat 520 has a spherical shape matching the spherical shape of the outer surfaces 30a, 30 of the head 3' and is configured to receive an outer surface portion of the head 3' which extends from the groove 33 to some extent beneath the greatest diameter E when the head is in the upper seat 520. As the head 3 is somewhat compressible, the head can be held in the upper seat 520 by friction. At an end of the upper seat 520 towards the first end 5a, an annular inner protrusion 521 is formed that narrows the passage 50'. The protrusion 521 is configured to engage the groove 33 when the head 3' is in the upper seat 520. Moreover, the protrusion 521 may have a flat bottom surface which faces the second end 5b to form a stop when engaging the groove 33 of the head 3'. By means of the circumferential protrusion 521, the insertion position for the head is defined. From the protrusion 521, the passage 50' may widen to a region with substantially constant diameter.

In this embodiment, a diameter of the inner thread 56 may be increased compared to the first embodiment to receive a slightly larger fixation member. A groove in the inner wall below the thread as in the first embodiment is not necessary, as this embodiment lacks a pressure member. It shall be noted that the recess 54' for receiving the rod 100 has a channel diameter that substantially corresponds to the diameter of the rod or is only slightly greater, so that the rod 100 is guided in the recess 54'. The size of the accommodation space 500 and the depth of the substantially U-shaped recess 54' is such that when the head 3' rests in the lower seat 52' in the pivot position, the apex of the upper spherical surface 30a is above a bottom of the substantially U-shaped recess 54' in the axial direction to be engaged by a bottom surface of the rod 100 to exert pressure onto the head 3' as shown for example in FIGS. 37b and 37c.

Figure 36D:
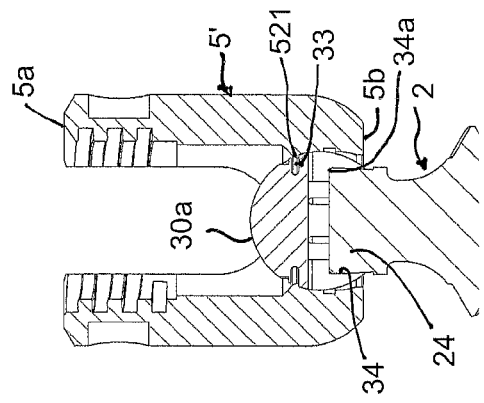
FIGS. 36a to 36d show cross-sectional views of assembling the bone anchoring device of FIGS. 26 and 27.
Figure 36C:
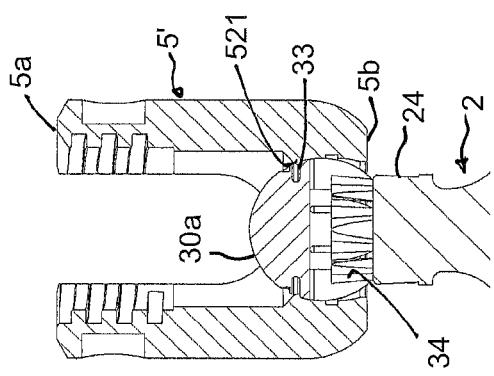
Figure 36B:
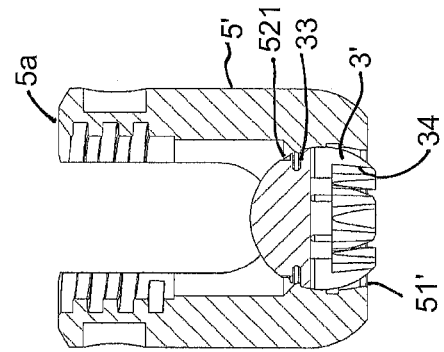
Figure 36A:
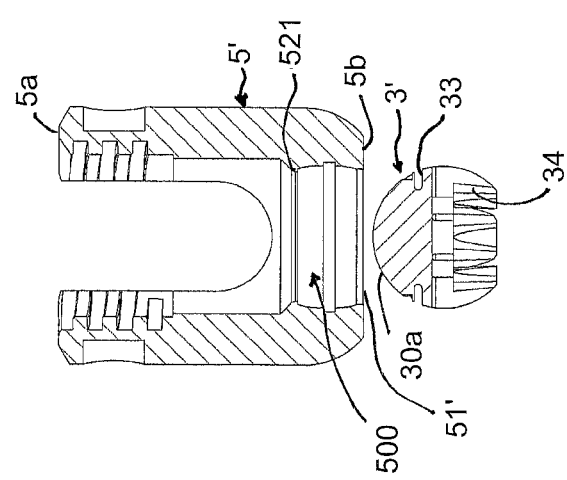

The assembly of the head 3' and the receiving part 5' is illustrated in FIGS. 36a to 36d. First, as shown in FIG. 36a, the head 3' is oriented such that the upper spherical surface 30a faces towards the opening 51' of the receiving part 5'. The head 3' is then introduced through the opening 51' into the accommodation space 500. To achieve this, the head 3' is slightly compressed to pass through the opening 51': As shown in FIG. 36b, the head 3' can enter the upper seat 520 until the annular protrusion 521 engages the lower portion of the groove 33, thereby preventing further upward movement. This is the insertion position for the shank. The head 3' is held in the upper seat 520 additionally by friction, so that the head cannot move by itself out of the insertion position into the pivot position. Thereafter, as depicted in FIG. 36c, the shank 2 can be inserted with the engagement portion 24 spreading apart the lower portion of the head 3' to enter the recess of the counterpart engagement portion 34. Finally, the engagement portion 24 of the shank 2 abuts against the stop 34a and the shank 2 is held by friction within the head 3' as depicted in FIG. 36d. Due to the stop provided by the annular protrusion 521, the head is prevented from moving out of the receiving part in the direction towards the first end 5a during insertion of the shank.

Referring to FIGS. 37a to 37c, once the receiving part 5' with head 3' is mounted to the shank 2, the head 3' is moved out of the insertion position into the lower seat 52'. As the protrusion 521 is rounded towards the first end 5a, the protrusion can easily move out of the groove 33. In FIG. 37a, the axis of the shank 2 and the central longitudinal axis C of the receiving part 5' are coaxial. Then, as shown in FIG. 37b, the receiving part 5' can be pivoted relative to the shank 2 and may be held in such a pivot position through friction in the lower seat 52'. Finally, as depicted in FIG. 37c, the rod is inserted into the substantially U-shaped channel 54' and the fixation member 7 is screwed between the legs 55 of the receiving part 5'. When the fixation member 7 is tightened, the fixation member presses onto the rod and the rod 100 presses in turn onto the spherical surface 30a of the head 3' to lock the rod and the head.

It shall be noted that, as in the first embodiment, in clinical use, the shank can be first inserted into bone and the pre-assembled receiving part 5' with head 3' can be mounted onto the shank, or alternatively, the bone anchoring device including the shank 2, the head 3' and the receiving part 5' can be pre-assembled and then inserted into bone. In any case, the drive structure 31' is accessible to a tool through the passage 50' and provides a large drive surface for applying high torques.

Further modifications of the above described embodiments are also conceivable. While the receiving part and the pressure member are shown as monolithic members, they can also be made up of two or more parts. For the shank all kinds of shanks can be used, such as partially threaded shanks, nails, cannulated shanks and various other shanks. It may be conceivable that the engagement portion of the shank has a recess and the counterpart engagement portion of the head includes a projection for engaging the recess of the shank. Various other drive structures for the engagement portion of the shank or the drive structure of the head may also be implemented.

The position indication structure can be designed so as to indicate a predefined angle other than the zero angle.

The pressure member may have legs that extend above the rod so that a two-part fixation member can be used. In such a two-part fixation member, for example, an inner fixation member is configured to act on the rod and an outer fixation member is configured to act on the legs of the pressure member.

While the rod is shown as a cylindrical rod, the rod may also have any other cross-section. The rod support surface can be cylindrical or flat, or have any other suitable contour for supporting the rod.

In addition, the particular features, structures or characteristics of one embodiment may be combined with those of other embodiments in any suitable manner to produce a multiplicity of further embodiments. Particular shapes of the elements are also not limited to the specific shapes shown in the drawings, but may vary as well.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An anchoring element comprising:
   a shank having a first end and an opposite second end below the first end that is configured to anchor to bone, and a longitudinal axis that extends between the first and second ends; and
   a separate head that is connectable to the shank, the head comprising an exterior surface with a spherically-shaped section and defining an opening for inserting the shank;
   wherein when the head and the shank are connected to one another, the spherically-shaped section of the exterior surface of the head includes a greatest diameter of the sphere measured in a direction perpendicular to the longitudinal axis, and the second end of the shank extends out of the opening, while the shank remains spaced apart in a direction of the longitudinal axis from an axial position of the spherically-shaped section of the head forming the greatest diameter of the sphere.

2. The anchoring element of claim 1, wherein the spherically-shaped section of the head forming the greatest diameter.

3. A bone anchoring device comprising the anchoring element of claim 1, and a receiving part that defines an accommodation space for receiving the head in a pivotable manner.

4. The bone anchoring device of claim 3, wherein the head is connectable to the receiving part prior to connecting the shank to the head.

5. The bone anchoring device of claim 3, further comprising a pressure member configured to exert pressure on the head to lock the head in the accommodation space.

6. The bone anchoring device of claim 3, wherein the head is configured to be held in the receiving part by friction.

7. The anchoring element of claim 1, wherein the head further comprises a tool engagement surface for engaging a drive tool.

8. The anchoring element of claim 1, wherein when the head and the shank are connected to one another, a length of the shank measured from the first end to the second end is greater than a greatest length of the head measured in a direction of the longitudinal axis.

9. The anchoring element of claim 1, wherein the head comprises an abutment configured to prevent further advancement of the shank into the head, the abutment being located axially between the opening and the axial position of the spherically-shaped section of the head forming the greatest diameter of the sphere.

10. An anchoring element comprising:
    a shank having a first end with a first engagement surface configured to engage a drive tool and an opposite second end below the first end that is configured to anchor to bone, and a longitudinal axis that extends between the first and second ends; and
    a separate head that is connectable to the shank, the head comprising an exterior surface with a spherically-shaped section and a second engagement surface configured to engage a drive tool, and defining an opening for inserting the shank in a direction of the longitudinal axis while a rotational orientation of the shank and the head relative to one another remains constant;
    wherein when the head and the shank are connected to one another, the head is configured to engage the first engagement surface of the shank to hold the connection between the shank and the head, and to restrict access by a drive tool to the first engagement surface of the shank.

11. The anchoring element of claim 10, wherein when the head and the shank are connected to one another, the head blocks a drive tool from accessing the first engagement surface along a direction of the longitudinal axis.

12. The anchoring element of claim 10, wherein an engagement portion of a drive tool that is configured to engage the first engagement portion of the shank is different from an engagement portion of a drive tool that is configured to engage the second engagement portion of the head.

13. The anchoring element of claim 10, wherein when the head and the shank are connected to one another, an end face at the first end of the shank is recessed relative to an end of the head opposite the opening.

14. A bone anchoring device comprising:
    a shank for anchoring to bone;
    a separate head that is connectable to the shank;
    a receiving part that defines an accommodation space configured to receive the head in a pivotable manner; and
    a pressure member comprising a rod contacting surface at a first end, a head contacting surface at a second end that is configured to exert pressure on the head to lock the head in the accommodation space, and a central axis extending between the first and second ends;
    wherein when the head and the pressure member are outside of the receiving part and are free from any outside forces acting thereupon, the pressure member is configured to engage the head to releasably hold the head against axial movement away from the pressure member, while the pressure member remains spaced apart from a greatest diameter of the head measured in a direction perpendicular to the central axis.

15. The bone anchoring device of claim 14, wherein when the head and the pressure member are held together, the head and the pressure member are insertable into the receiving part together.

16. The bone anchoring device of claim 14, wherein the head comprises an exterior surface with a spherically-shaped section.

17. The bone anchoring device of claim 14, wherein the head is connectable to the receiving part prior to connecting the shank to the head.

18. The bone anchoring device of claim 14, wherein the head is configured to be held in the receiving part by friction.

19. The bone anchoring device of claim 14, wherein one of the head or the pressure member defines a groove and the other of the head or the pressure member comprises a portion configured to extend into the groove to engage the head.

20. The bone anchoring device of claim 14, wherein when the head and the pressure member are in the receiving part, the engagement between the head and the pressure member is configured to hold the head at a first angular position relative to the receiving part, and is releasable such that the receiving part and the pressure member are pivotable together away from the first angular position relative to the head.

* * * * *